United States Patent
Lee et al.

(10) Patent No.: US 7,811,603 B2
(45) Date of Patent: Oct. 12, 2010

(54) MICROFLUIDIC DEVICE FOR FORMING MONODISPERSE LIPOPLEXES

(75) Inventors: Abraham Phillip Lee, Irvine, CA (US); Albert Tsung-Hsi Hsieh, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/746,024

(22) Filed: May 8, 2007

(65) Prior Publication Data

US 2007/0264320 A1 Nov. 15, 2007

Related U.S. Application Data

(60) Provisional application No. 60/746,840, filed on May 9, 2006.

(51) Int. Cl.
*A61K 9/127* (2006.01)
(52) U.S. Cl. .......................... 424/450; 264/4.1
(58) Field of Classification Search ................. 424/450; 977/907; 514/44; 264/401
See application file for complete search history.

(56) References Cited

U.S. PATENT DOCUMENTS

2004/0068019 A1 * 4/2004 Higuchi et al. ................. 516/9

FOREIGN PATENT DOCUMENTS

| WO | WO/96/32116 | * | 10/1996 |
| WO | WO 2004/071638 | * | 8/2004 |

OTHER PUBLICATIONS

Tan et al Lab Chip, 2005, 5, 1178-1183.*
Nisisako et al SICE, 2002, 957-959.*
Atencia et al ,Nature, 2005, 437: 648-655.*
Bertsch et al Proceedings of the IEEE 14th annual international conference on microelectro mechanical systems, MEMS 2001, Interlaken, Switzerland Jan. 21-25, 2001, pp. 507-510.*
Fisher et al Presented on Sep. 26-30, 2004 published in 2005, pp. 647-649, at 8th International Conference on Miniaturized Systems for Chemistry and Life Sciences, Malmo, Sweden.*
Rousselle et al Journal of Biological Chemistry, 1996, 271, 726-735.*
Nichols Lab Chip, 2006, 242, 6, 242-246, available online Dec. 8, 2005.*
Song et al Lab Angew. Chem. Int. Ed. 2003, 42, No. 767-772.*
TIce et al Langmuir 2003, 19, 9127-9133.*
Bringer et al Philosophical transactions R. Soc. Lond. Series A, Mathematical, physical, and engineering sciences, (May 15, 2004) vol. 362, No. 1818, pp. 1087-1104.*
Duffy, David C., et al., "Rapid Prototyping of Microfluidic Systems in Poly(dimethylsiloxane)," Anal. Chem. 1998, 70, 4974-4984.
Zelphati, O, et al., "Stable and Monodisperse Lipoplex Formulations for Gene Delivery," Gene Therapy (1998) 5, 1272-1282.

* cited by examiner

*Primary Examiner*—Deborah Crouch
*Assistant Examiner*—Anoop Singh
(74) *Attorney, Agent, or Firm*—Vista IP Law Group LLP (57) ABSTRACT

A method for forming monodisperse lipoplex assemblies includes providing a microfluidic device having a main microfluidic channel coupled to first and second reactant inlet channels. The first inlet channel is used to deliver a cationic lipid to the main channel while the second channel is used to deliver a nucleic acid. A droplet generation zone is provided in the main channel at the intersection of first and second carrier channels that contain a hydrophobic fluid. The cationic lipid, nucleic acid, and the hydrophobic fluid are then pumped through the device. In the droplet generation zone, shear force from the hydrophobic fluid pinches off droplets. The cationic lipid and nucleic acid are mixed in the generated droplets as the droplets move within a mixing region. A plurality of splitting channels may be coupled to the outlet of the device to produce smaller, monodisperse droplets having picoliter volumes.

10 Claims, 7 Drawing Sheets

MICROFLUIDIC DEVICE FOR FORMING MONODISPERSE LIPOPLEXES

RELATED APPLICATIONS

This Application claims priority to U.S. Provisional Patent Application No. 60/746,840 filed on May 9, 2006. The above-noted Application is incorporated by reference as if set forth fully herein.

FIELD OF THE INVENTION

The field of the invention generally relates to microfluidic devices. More particularly, the field of the invention relates to microfluidic devices capable of generating a complex of nucleic acid (e.g., DNA) and a cationic lipid to form a non-viral liposomal carrier having a small size distribution. The device and method may be used as a pico-liter microreactor and microincubator for improving gene transfection and/or gene therapy

BACKGROUND OF THE INVENTION

There is a growing need to develop non-viral based carriers for the delivery of drugs, plasmic DNA, shRNA, and the like for pharmaceutical and therapeutic applications. Cationic lipid based liposomal carriers are an attractive non-viral delivery modality. Advantages of liposomal vectors include safety, lack of immunogenicity, ability to package large DNA molecules, and ease of preparation. For example, cationic lipid/DNA complexes may be used for in vitro and in vivo gene delivery. These lipid-gene complexes may thus be used in various gene therapy applications.

The size of the cationic and DNA complexes, which are referred to herein as "lipoplexes," dictates the efficiency of gene transfection. Conventionally, lipoplex formation was accomplished by hand shaking or vortexing a mixture of cationic lipids and DNA. Unfortunately, these conventional techniques to generate lipoplexes have largely produced lipoplexes having characteristics that are irreproducible. In addition, conventional preparation processes such as hand shaking and vortexing suffer from the problem that the resulting lipoplexes have a large size distribution. Because the size of the individual lipoplex particles affects the rate of transfection, a population of lipoplexes having a broad array of sizes will adversely affect the overall efficiency of gene transfection.

Various parameters are known to affect the lipoplex sizes which include, the order of mixing of the cationic liquid and the DNA, the rate of mixing, and the mixture incubation time. The lack of control over the biophysical parameters that affect lipoplex generation is thus a barrier to consistently obtaining stable and monodisperse lipoplex formulations. There thus is a need for a methods and devices that are able to efficiently formulate monodisperse lipoplex assemblies. The device and method should be able to rapidly produce monodisperse lipoplex assemblies in a narrow size distribution. Moreover, there is a further desire and need to reduce the size of the lipoplex assemblies that are generated. By reducing the size of the lipoplex assemblies generated, this will generally reduce the amount of incubation time needed to form the complete assemblies since the incubation time is generally proportional to the size of the lipoplexes due to aggregation. Moreover, there is a need for a microfluidic-based device that can integrate multiple processing steps such as mixing and incubation into a relatively small device.

SUMMARY OF THE INVENTION

According to one embodiment of the invention, a method of forming monodisperse lipoplexes includes providing a microfluidic device having a main channel including a droplet generation zone, the droplet generation zone comprising an intersection between the main channel and first and second carrier channels configured to receive a hydrophobic fluid, the microfluidic device further comprising first and second inlet channels coupled to the main channel at a region upstream from the droplet generation zone. The method further includes providing a first reactant in fluid communication with the first inlet channel, the first reactant comprising a cationic lipid and providing a second reactant in fluid communication with the second inlet channel, the second reactant comprising a nucleic acid. A hydrophobic fluid is provided in fluid communication with the first and second carrier channels. The first and second reactants and the hydrophobic fluid are then flowed (e.g., pumped) into the droplet generation zone so as to generate a plurality of lipoplex droplets.

In another aspect of the invention, a microfluidic device for forming monodisperse lipoplex assemblies includes a substrate including a main microfluidic channel coupled to first and second reactant inlet channels, the main microfluidic channel including droplet generation region, the droplet generation zone comprising an intersection between the main microfluidic channel and first and second carrier channels configured to receive a hydrophobic fluid. The device also includes a mixing region disposed downstream of the droplet generation zone and a plurality of branch channels coupled to an output of the mixing region.

In still another aspect of the invention, a system for generating monodisperse lipoplexes includes a microfluidic device including a main microfluidic channel coupled to first and second reactant inlet channels, the first reactant inlet channel being operatively connected to a source of cationic lipid, the second reactant inlet channel being operatively connected to a source of nucleic acid, the main microfluidic channel including droplet generation region comprising an intersection between the main microfluidic channel and first and second carrier channels configured to receive a hydrophobic fluid. The device includes a mixing region disposed downstream of the droplet generation zone and pumping means configured for flowing the cationic lipid and nucleic acid into the first and second reactant inlets. The system also includes secondary pumping means configured for flowing the hydrophobic fluid into the first and second carrier channels. The system includes a plurality of branch channels coupled to an output of the mixing region.

DETAILED DESCRIPTION OF THE ILLUSTRATED EMBODIMENTS

Figure 1:
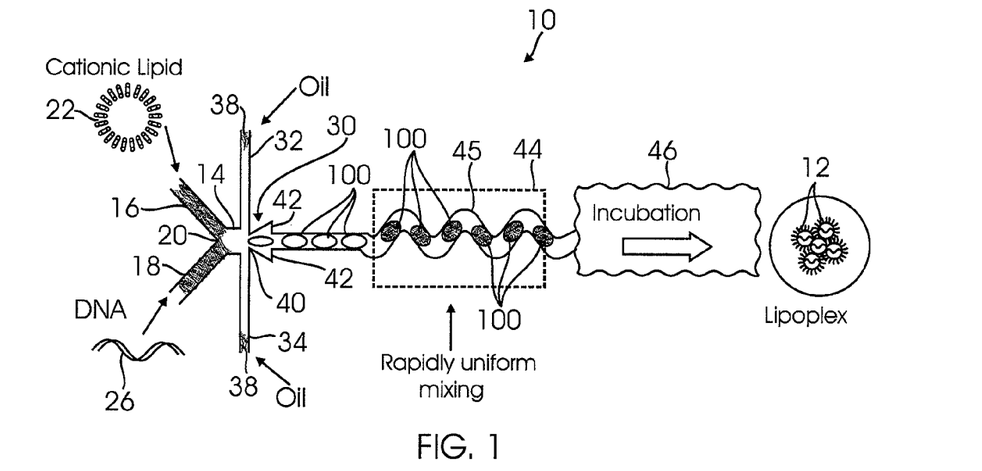
FIG. 1 schematically illustrates a microfluidic device for generating monodisperse lipoplex assemblies according to one embodiment.
Figure 2:
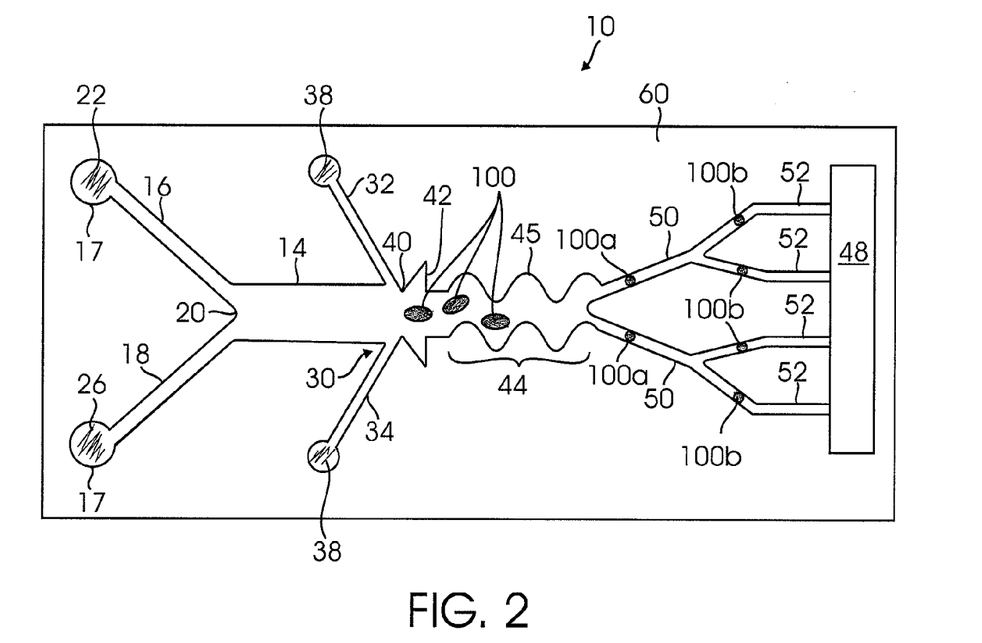
FIG. 2 illustrates a microfluidic device of the type illustrated in FIG. 1 formed in a substrate. Also illustrated are branch channels used to split droplets into smaller volumes along with a downstream collection chamber or reservoir.

FIG. 1 illustrates a microfluidic device 10 for generating monodisperse lipoplex assemblies according to one embodiment. As used herein, the term "lipoplex assemblies" generally refers to the complex formed between a cationic lipid and nucleic acid after mixing and incubation. For example, the lipoplex assemblies may include one or more vesicles 12 that contain nucleic acid in an interior portion thereof. FIG. 1 illustrates a main microfluidic channel 14 that is connected to a first inlet channel 16 and a second inlet channel 18 via a junction 20. The first inlet channel 16 as illustrated in FIG. 1 is configured to receive a cationic lipid 22 (as illustrated in FIG. 2). The first inlet channel 16 may be coupled to a reservoir or chamber 17 that contains the cationic lipid 22. Alternatively, the first inlet channel 16 may be coupled via tubing 22 (as illustrated in FIG. 2 and which may be connected to the reservoir 17) or the like that is connected to a source of cationic lipid 22.

Referring back to FIG. 1, the second inlet channel 18 is configured to receive a nucleic acid 26. As seen in FIG. 1, the nucleic acid 26 is DNA but it may include other types of nucleic acid such as RNA, shRNA, and the like. The nucleic acid 26 may be injected in any number of forms including double stranded, single stranded, fragmented, or as a plasmid. Like the first inlet channel 16, the second inlet channel 18 may be coupled to a reservoir or chamber 17 (as seen in FIG. 2) that contains the nucleic acid 26. Alternatively, the second inlet channel 18 may be coupled via tubing 22 (as illustrated in FIG. 2 and which may be connected to the reservoir 17) or the like that is connected to a source of nucleic acid 26.

As seen in FIG. 1, the main microfluidic channel 14 includes a droplet generation zone 30. The droplet generation zone 30 is formed at the junction or intersection of the main microfluidic channel 14 with first and second carrier channels 32, 34. The first and second carrier channels 32, 34 are configured to receive a hydrophobic liquid 38. The hydrophobic liquid 38 is a hydrophobic fluid such as oil but may include other liquids that are immiscible in an aqueous phase. This may include oils or organic solvents. The oil may include, for example, silicon oil, mineral oil, or other water immiscible oils. The hydrophobic fluid 38 preferably contains a surfactant that prevents the individual droplets 100b from breaking in the reservoir 48. The amount and nature of the surfactant may vary depending on the type of hydrophobic fluid 38. For example, if mineral oil is used, sorbitan monooleate in a concentration of around 0.1 to 2.0 percent (on a volume basis) may be added.

Figure 8:
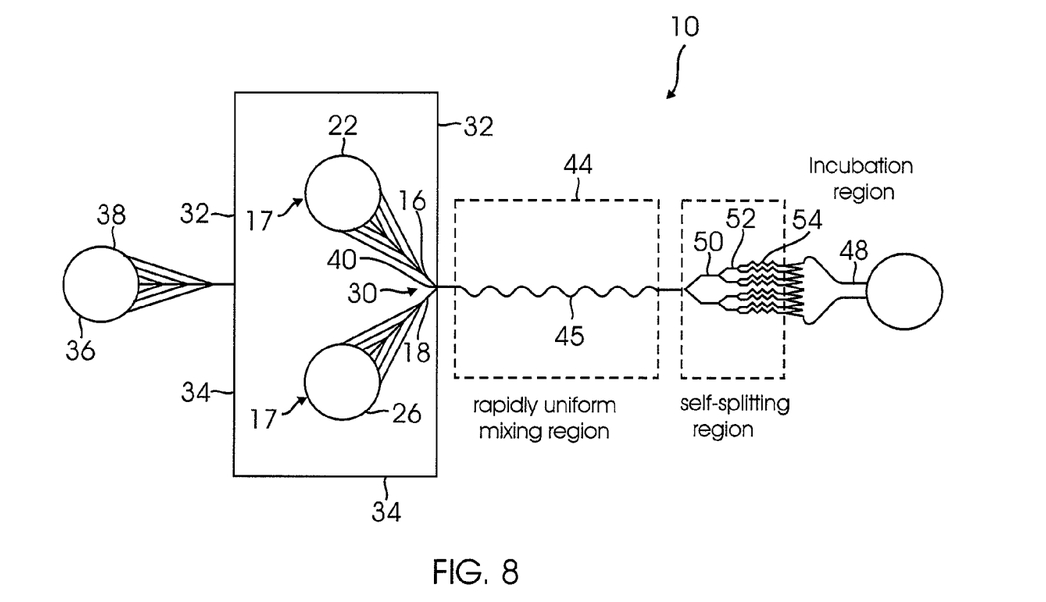
FIG. 8 schematically illustrates a microfluidic device for generating monodisperse lipoplex assemblies according to another embodiment.

As seen in FIG. 1, the first and second carrier channels 32, 34 interface with the main channel 14 on opposite sides. This orientation permits formation by pinching in the droplet generation zone 30. In this regard, the droplet generation zone 30 may include a pinch junction 40 that is formed by reducing the cross-sectional area of the channel 14 in the droplet generation zone 30. The pinch junction 40 may have a width that is several microns thinner than the corresponding width upstream of the pinch junction 40 (e.g., pinch junction having a width of around 50 μm). For instance, the pinch junction 40 may have a width within the range of about 5 μm to about 250 μm. As seen in FIG. 1, the pinch junction 40 may include flared regions 42. The first and second carrier channels 32, 34 may be connected separately to sources of the hydrophobic fluid 38 as illustrated in FIG. 2 or, alternatively, the first and second carrier channels 32, 24 may be joined at a common inlet or reservoir 36 as illustrated in FIG. 8.

Figure 5:
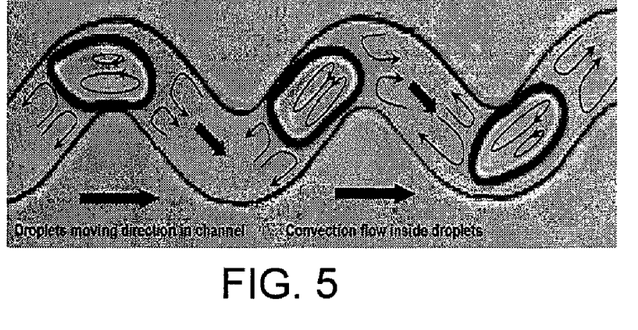
FIG. 5 illustrates an annotated view of a photographic image taken of droplets passing through the mixing region of the device. The chaotic advection mixing that occurs with the droplets is illustrated.

As seen in FIG. 1, the mixture of the cationic lipid 22 and the nucleic acid 26 are pinched off into droplets 100 within the droplet generation zone 30. The droplets 100 continue within the main channel 14 and, in one aspect of the invention, enter a mixing region 44. It should be pointed out that once inside the droplet 100, the cationic lipids 22 and nucleic acid vector 26 start to mix instantly due to the chaotic advection resulting from the droplet moving in the sawtooth-shaped channel. The mixing region 44 includes a curved or tortuous microfluidic channel 45. Mixing of the cationic lipid 22 and the nucleic acid 26 is accelerated in the mixing region 44 because of the convection flow developed within the tortuous microfluidic channel 45. The flow within the mixing region 44 induces convective flow within the actual droplets 100, thereby aiding in mixing the cationic lipid 22 and the nucleic acid 26. FIG. 5 shows a photographic image of droplets 100 undergoing convective mixing within the mixing region 44 of the device 10.

Still referring to FIG. 1, the tortuous channel 45 in the mixing region 44 may terminate into an incubation region 46. The incubation region 46 may include a chamber or reservoir 48 into which the mixing region 44 terminates (as seen in FIG. 2). In one aspect, the mixing region 44 include a single channel 45 that terminates into the incubation chamber 48. In another, alternative aspect, as illustrated in FIG. 2, the channel of the mixing region 44 terminates into a plurality of first branch channels 50. For example, the one channel from the mixing region 44 may terminate into two branch channels 50. In one aspect, the first branch channels 50 are then split again into second branch channels 52.

Figure 7:
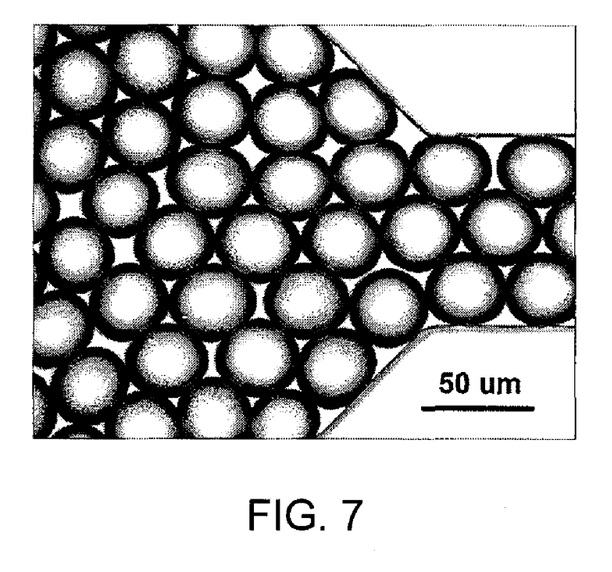
FIG. 7 illustrates a photographic image showing mixtures of cationic lipids and DNA incubating in monodisperse picoliter volume droplets which serve as an incubator for lipoplex formation.

In the devices 10 of FIGS. 1 and 2, the cationic lipid 22 and nucleic acid 26 are uniformly distributed in the formed droplets 100. In the embodiment of FIG. 2, the primary droplet 100 is first split into two (2) smaller droplets 100a in the first branch channels 50. Each of the smaller droplets 10a is then split again into even smaller droplets 100b in the second branch channels 52. Thus, a single main or primary droplet 100 is split into four (4) smaller droplets 100b using the first and second branch channels 50, 52. The resulting droplets 100b have volumes measured in picoliters. The droplets 100b may range in size from around 30 μm (volume=0.942 picoliters) to around 100 μm (volume=~10.47 picoliters). The splitting feature increases the droplet generation rate. The smaller-sized droplets have shorter lipoplex formulation times and also permit the formation of larger quantities of lipoplex that can be used, for example, for later transfection applications. Generally, the incubation time for cationic lipid/DNA mixtures is proportional to the size of the lipoplexes due to aggregation. Here, the amount of time needed for incubation is reduced because of the small size of the droplets 100b. FIG. 7 illustrates a photographic image of a mixture of cationic lipids and DNA molecules that are incubating in a monodisperse picoliter-sized droplet which serves as a "microincubator" for lipoplex assembly formation.

Figure 3:
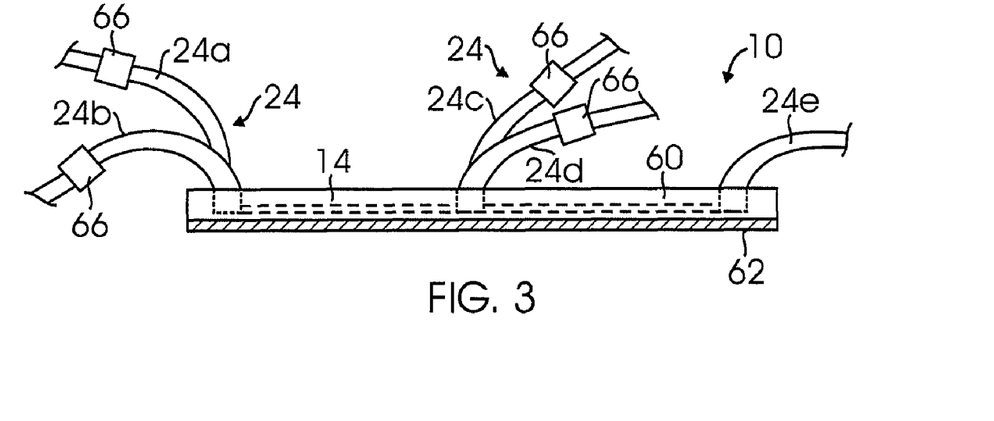
FIG. 3 illustrates a side view of a microfluidic device including the substrate bonded to the glass cover. Also illustrated are conduits (e.g., tubes) that connect to the various inlets and outlets of the device and are used to pump fluid through the device.

Referring to FIGS. 2 and 3, the device 10 is preferably formed on a substrate 60. For example, the substrate 60 may include polydimethylsiloxane (PDMS) and sealed with a glass cover 62 (FIG. 3). In an alternative aspect, the cover 62 may also be formed from PDMS. Prior to adhering the glass cover 62, both the substrate 60 (e.g., PDMS replica) and the glass cover 62 may be treated with oxygen plasma (~one minute) and then sealed in an irreversible manner. The oxygen plasma treatment makes the surface of the PDMS and glass cover 62 hydrophilic. As seen in FIG. 3, a conduit 24 such polyethylene tubing may be inserted into the various inlets of the device 10 to provide fluid communication from the various fluid sources to their respective inputs. For example, in FIG. 3 tubing 24a, 24b connect to the first and second inlet channels 16, 18 respectively (or via reservoirs 17). Likewise, tubing 24c, 24d connects the first and second carrier channels 32, 34, respectively. Tubing 24e may connect to the reservoir 48 of the device 10 to remove accumulated fluid and lipoplexes. As seen in FIG. 3, pumps 66 such as syringe pumps may be used to drive the various fluids into the device 10. Of course, other types of pumping devices may be used to pump or flow fluid through the device 10. For example, acoustic pumps, magneto-hydrodynamic pumps, electrophoretic pumps, dielectrophoretic pumps, and the like may be used to pump fluid through the device 10.

In the devices 10 illustrated in FIGS. 1 and 2, the cationic lipid 22 and nucleic acid 16 may be pumped at rate this around one-half the rate of flow of the hydrophobic fluid 38. For example, the cationic lipid 22 and nucleic acid 16 may be pumped within the device 10 at a rate of around 1 microliter/minute while the hydrophobic fluid 38 is pumped at a rate of around 2 microliter/minute.

The various microfluidic features may be formed, for example, on PDMS such as SU-8 using soft lithography techniques. Soft lithography using PDMS techniques is a known method of forming microfluidic devices. For example, the publication by Duffy et al., *Rapid Prototyping of Microfluidic Systems in Poly(dimethylsiloxane)*, Anal. Chem., 70 (23), 4974-4984 (1998) describes one such process. The above-identified publication is incorporated by reference as if set forth fully herein.

Figure 4:
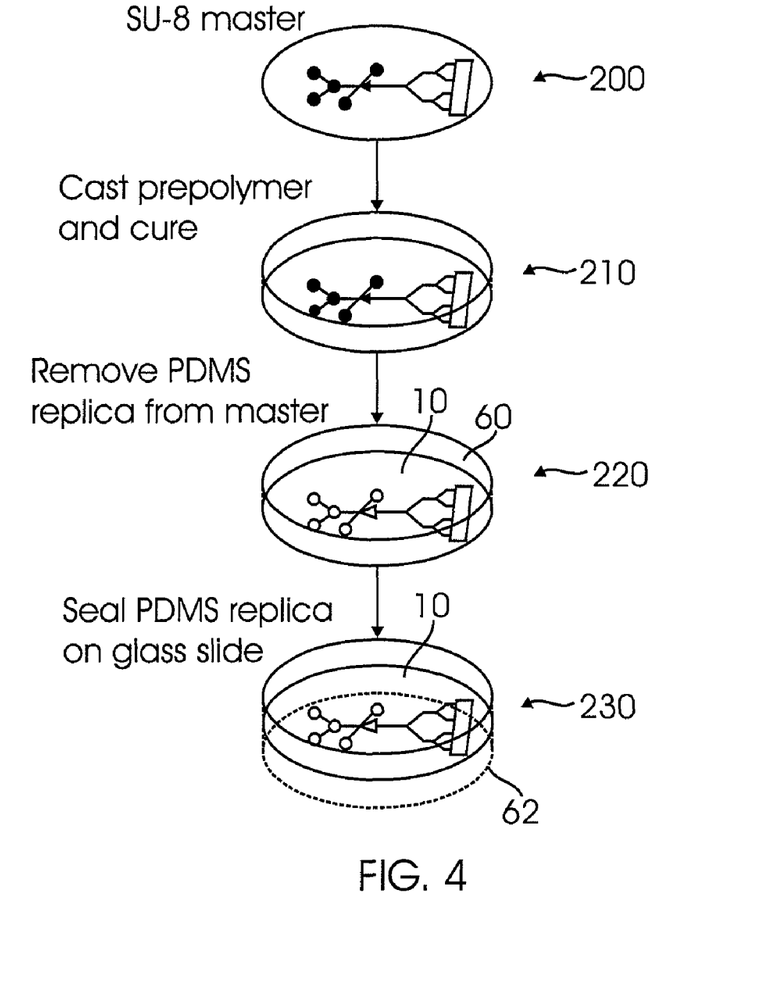
FIG. 4 illustrates a process of forming the microfluidic device in a PDMS-based substrate according to one embodiment.

FIG. 4 illustrates one exemplary technique that can be used to form the device 10. In step 200, a SU-8 master is provided which has the various features formed therein. These include the inlet channels 16, 18, carrier channels 32, 34, droplet generation zone 30, mixing region 44, branch channels 50, 52, and reservoir 48. As seen in step 210, a PDMS pre-polymer is then cast over the SU-8 master and is allowed to cure. The PDMS replica which forms the substrate 60 is then removed from the SU-8 master in step 220. The PDMS replica in the substrate 60 is then permanently sealed to a glass cover 62.

With reference to the device of FIGS. 1-3, the width and height of the channels 14, 16, 18, 32, 34, 50, 52 are typically on the order of several microns to tens of microns in height. For example, the height of the channels 14, 16, 18, 32, 34, 50, 52 may be within the range of around 10 μm to around 250 μm (e.g., 100 μm). The width of the various channel 14, 16, 18, 32, 34, 50, 52 is typically on the tens or hundreds of microns. For example, the width of the first and second inlet channels 16, 18 may be within the range of around 25 μm to around 100 μm (e.g., 50 μm). The width of the first and second carrier channels 32, 34 may be within the range of 25 μm to around 100 μm. The width of the main channel 14 (excluding the pinch junction 40) may be around μm 50 μm to around 200 μm (e.g., 120 μm).

The width of the tortuous-shaped mixing channel 45 may be around 100 μm to around 200 μm (e.g., 140 μm). Finally, the first set of branch channels 50 typically have a width that is less than the width of the upstream channel. For example, the first branch channels 50 may have a width of around 80 μm to around 120 μm (e.g., 100 μm). The second set of branch channels 52 again have a width that is less than the width of the upstream branch channels 50 or around 50 μm to around 90 μm (e.g., 70.5 μm). Finally, in certain embodiments like that illustrated in FIG. 9, a third set of branch channels 54 may be reduced in width even further. For example, the third branch channels 54 may have a width in the range of around 30 μm to around 60 μm (e.g., 50 μm).

A device 10 of the type illustrated in FIGS. 1-3 was designed and tested regarding the ability to form monodisperse lipoplex assemblies. The test was performed to, among other things, test the ability of the device 10 to produce picoliter sized lipoplex assemblies that have a relatively narrow distribution of sizes (i.e., monodispersed). In the experiment, a device 10 of the type illustrated in FIGS. 1-3 was pumped (via syringe pumps) with a cationic lipid 22 and nucleic acid 26. The cationic lipid 22 included diluted 1:1 (DOTMA/DOPE) liposome formulation of cationic lipids where DOTMA is N-[1-(2,3-dioleyloxy)propyl]-N,N,N-trimetylammonium chloride and DOPE is 1,2-Dioleoyl-sn-glycero-phosphatidylethanolamin (both available from Invitrogen of San Diego, Calif.) in Opti-MEM solution (available from Gibco BRL, San Diego). The nucleic acid 26 included DNA vector (eGFP-C3 vector (plasmid DNA)) in Opti-MEM solution. Both the nucleic acid 26 and the cationic lipid 22 were simultaneously injected via the first and second inlet channels 16, 18. The merged stream was then pinched-off by the shear force from the side oil streams via the first and second carrier channels 32, 42 in the droplet generation zone 30. The simultaneous injection of the nucleic acid 26 and the cationic lipid 22 contributed to generating the same number of cationic lipids and DNA molecules in each droplet and minimizing the lipoplex size difference.

Once inside the droplet, the cationic lipids 22 and the DNA vector 26 start to immediately mix due to the chaotic advection resulting from the droplet 100 moving within the mixing region 44. FIG. 5 illustrates an annotated photographic image of the formed droplets 100 undergoing mixing by convective flow as the droplet moves along the length of the mixing region 44.

Figure 6:
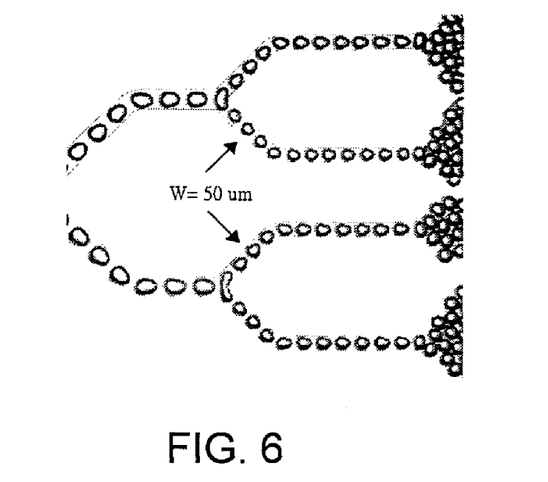
FIG. 6 illustrates a photographic image taken of the droplets located in the downstream branch channels or splitting channels.

FIG. 6 illustrates a photographic image taken of the droplets 100a, 100b located in the branch channels 50, 52. As seen in FIG. 6, a single main or primary droplet 100 (not shown in FIG. 6) is first split into two (2) smaller droplets and then subsequently into four (4) even smaller droplets. The smallest droplets 100*b* seen in FIG. 6 have a diameter of around 43 μm which translates into a volume of approximately 41.6 picoliters. The small volume or size of the droplets 100*b* reduces the cationic lipid 22 and nucleic acid 26 diffusion time and accelerates the formation rate of lipoplex assemblies.

FIG. 8 illustrates another embodiment of the device 10. In this embodiment, the hyrophobic fluid 38 is contained in a common inlet or reservoir 36 that then joins the first and second carrier channels 32, 34. In this embodiment, another set of splitting branch channels 54 is provided to further split or reduct the size of the droplets 100. In this embodiment a single drop is split into a total of eight (8) droplets. For example, the droplets may have a diameter of around 30 μm (~14.1 picoliter volume).

Figure 9:
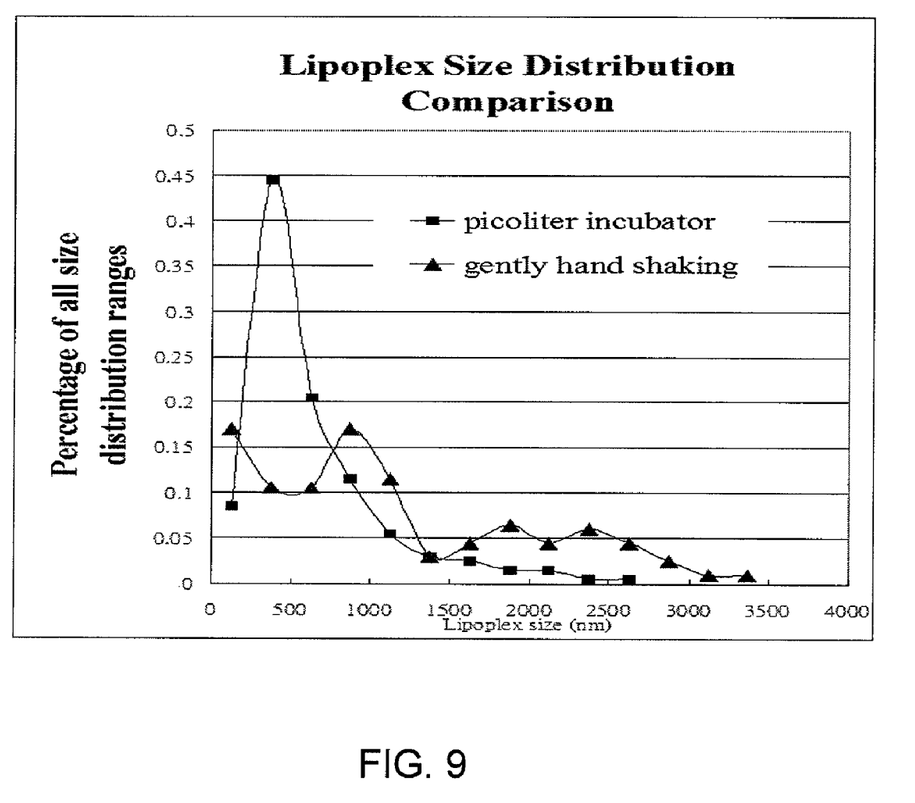
FIG. 9 illustrates a graph illustrating the lipoplex size distribution of lipoplex assemblies formed using the device described herein in addition to lipoplex assemblies formed using gentle hand shaking (conventional process). The solid line with rectangular-shaped data points represents the lipoplex assemblies prepared by the current invention and the solid line with triangular-shaped data points represents the lipoplex preparation by conventional hand-shaking method.

The device 10 is able to produce lipoplex assemblies in which the number of molecules of cationic lipid 22 and nucleic acid 26 are roughly the same. Because of this, lipoplex assemblies with a relatively narrow size distributions can be created. In this regard, the lipoplex assemblies are monodispersed. FIG. 9 is a graph illustrating the size distribution of lipoplex assemblies prepared by the device 10 illustrated in FIG. 8 and compared with the size distribution associated with conventional hand shaking techniques. Lipoplex size was measured using dynamic light scattering (DAWN HELEOS, Wyatt Technology Corporation, Santa Barbara, Calif.). As seen in FIG. 9, the lipoplex assemblies prepared by the device 10 show a narrower size distribution peak and smaller average size. For example, a substantial portion of the overall lipoplex assemblies have sizes under 500 nm. This also results in a smaller average size of the generated lipoplex assemblies in the device 10 as opposed to those generated by conventional hand shaking techniques.

Once the lipoplex assemblies are created in the device 10 and sufficiently incubated within the chamber or reservoir 48, they can be removed from the device 10 for further processing. For example, the lipoplex assemblies may be pumped or vacuumed out (via a pump or even syringe) using tubing 24*e* as illustrated in FIG. 3. The collected lipoplex assemblies may be added with a cellular media solution such as Opti-MEM solution. The lipolex assemblies may be stored in eppendorf vials and then spun in a centrifuge (2-4 minutes at 1000 rpm). The centrifuge process breaks the droplets so that the now-created lipoplexes can be recovered. The top-most oil phase may be removed from the epindorf vials thereby leaving the Opti-MEM solution containing the lipoplex. The liberated lipoplex can be removed, for example, via pipette and retained for further use/processing.

Figure 10:
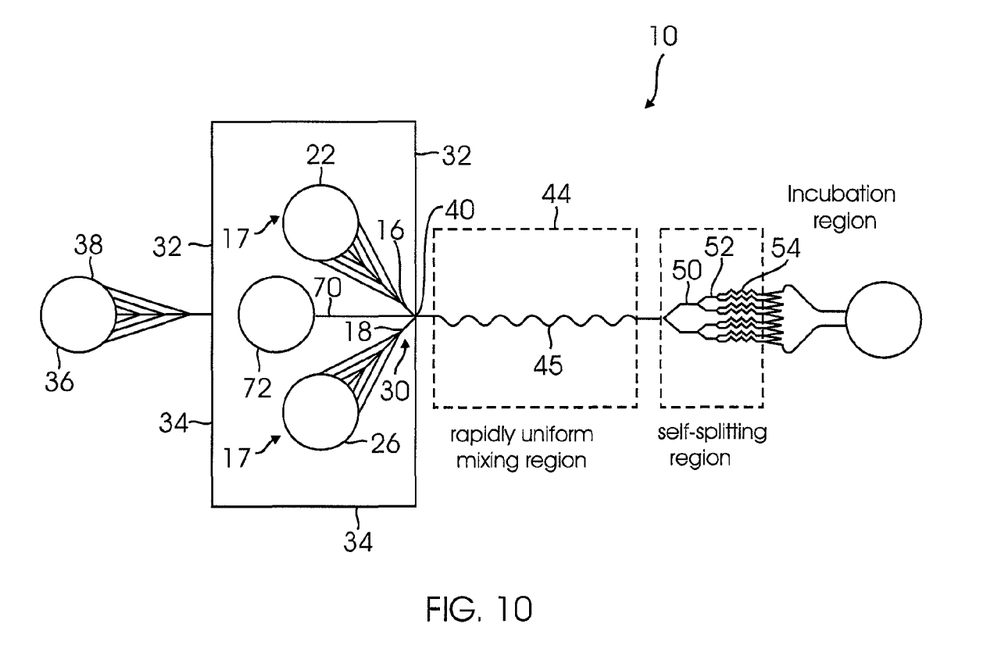
FIG. 10 schematically illustrates a microfluidic device for transfecting cells with lipoplex assemblies according to another embodiment.

FIG. 10 illustrates another embodiment of a device 10 according to the invention. The device 10 is similar to that illustrated in FIG. 8 with the exception that another (i.e., third) inlet channel 70 is provided. The inlet channel 70 may terminate in an optional reservoir or chamber 72. Alternatively, tubing or other conduits (not shown) may connect directly to the inlet channel 70 (or reservoir 72). The inlet channel 70 is configured to input cells into the device 10. The flow rates of the various reagents may be adjusted to create more or less cells per droplet. One exemplary flow rate is 2.0 μl/minute for the hydrophobic fluid 38 while the input flow rate for the cells, cationic lipid 22, and nucleic acid 26 is about 0.67 μl/minute.

In addition, as seen in FIG. 10, the fist and second inlet channels 16, 18 along with the carrier channels 32, 34 may be coupled to respective reservoirs 17, 36 via a plurality of narrow inlet channels (~20 μm) which serve as a PDMS fragment filter. PDMS fragments may be generated during punch-hole processes for tubing connections. The narrow inlet channels keep the PDMS fragments inside the reservoir 17, 36. If one channel (i.e., filter) is blocked, fluid will switch to another open one. Without the filter design, PDMS fragments generated during the hole punch process may easily to clog the channel at pinch-off point 40 and result in droplet generation problems. The same filter may also be used in connection with the reservoir 72 and inlet channel 70 use for the cells.

Conventionally, the transfection rate of nucleic acids (e.g., genes) into cells is restricted by the amount of gene carrier molecules. A low concentration of gene carriers that reach the cell membrane will result in a low transfection rate. The transfection rate can not typically be increased by raising the concentration of gene carriers because these carriers (i.e., cationic lipids) are toxic to the cell. The device in FIG. 10 overcomes this limitation by localizing the nucleic acid 26, cationic lipid 22, and cell within the generated droplets 100. This increases the local concentration of the lipoplex at the cell membrane surface without increasing the overall concentration of cationic lipids and DNA which would kill or otherwise harm the cells.

The cells are encapsulated along with the nucleic acid 26, and cationic lipid 22 are well-mixed in the mixing region 44 of the device 10. Because the droplets 100 are small (e.g., around 60 μm), the distance between the lipoplex and the cells are greatly reduced and the amount of time needed for the lipoplex to diffuse to reach the cell membrane surface is drastically reduced. Cellular uptake of DNA is thus increased. Certain cell lines like neural ells, leukemia cells, and primary cell lines are hard to transfect using liposomal-based carriers (e.g., typically lower than 20%). The devices 10 described herein, however, may be used to improve the transfection rate in these hard-to-transfect cell lines.

Figure 11:
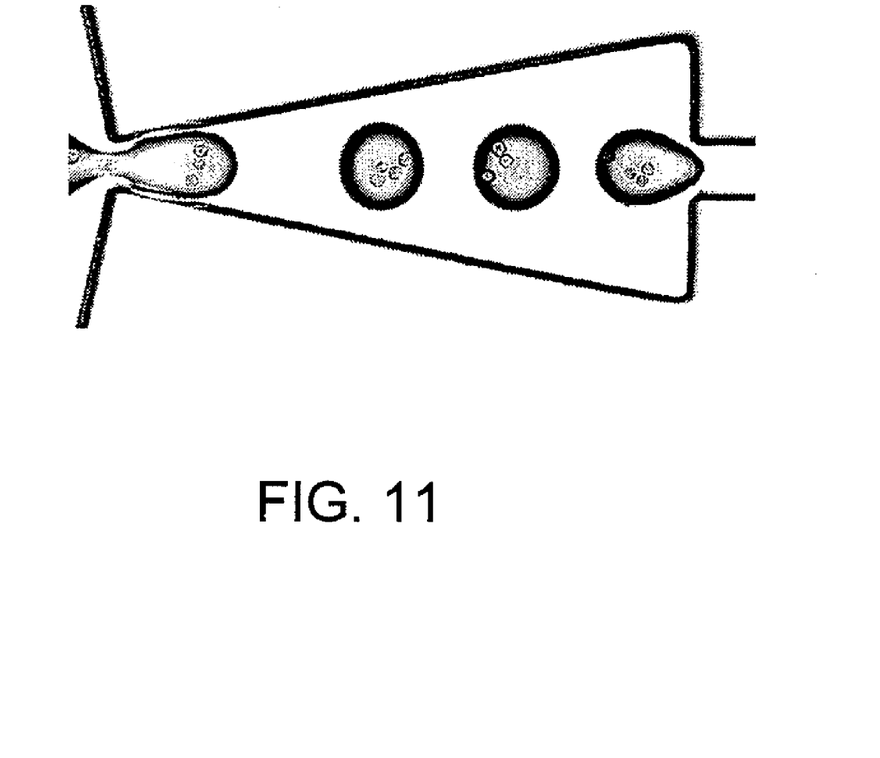
FIG. 11 illustrates a photographic image of the droplet generation zone of the device of FIG. 10. Cells were encapsulated in droplets for co-location transfection.
Figure 12:
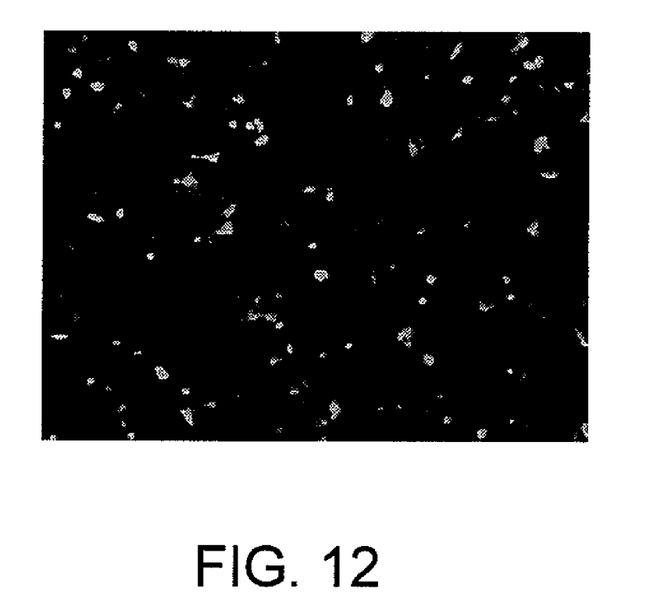
FIG. 12 illustrates a photographic image taken of the backside of the Petri dish which illustrates the distribution of transfected cells (represented in lighter areas).

FIG. 11 illustrates a photographic image of the droplet generation zone 30 of the device 10 of FIG. 10. Each generated droplet contains one or more cells that are encapsulated with the cationic lipid 22 and nucleic acid 26 (in this case DNA). In order to compare transfection rates, the incubated cells (U2OS cells) obtained from the device 10 of FIG. 10 were harvested and incubated on a Petri dish for about twenty four hours. The cells were transfected with eGFP-C3 plasmid DNA. Successful transfection could be monitored by the presence fluorescent green protein. FIG. 12 illustrates a photographic image taken of the backside of the Petri dish which illustrates the distribution of transfected cells (lighter areas).

The cells were removed from the Petri dish using trypsin-EDTA and then input to a fluorescent-activated cell sorter (FACS) device (Beckton-Dickinson Caliber FACS). The FACS device was used to count the number of transfected cells. The results showed an average transfection rate of around 50% which is much higher than conventional transfection rates involving this cell line. In this regard, the device 10 is able to co-localize gene transfection within the droplets 100. This is permits improved gene transfection rates of conventionally hard to transfer cell lines with a lower toxicity.

While embodiments of the present invention have been shown and described, various modifications may be made without departing from the scope of the present invention. The invention, therefore, should not be limited, except to the following claims, and their equivalents.

What is claimed is:

1. A method of forming monodisperse lipoplex assemblies, said lipoplex assemblies comprising a complex formed between a cationic lipid and a nucleic acid, the method comprising:

providing a microfluidic device having a main channel including a droplet generation zone, the droplet generation zone comprising an intersection between the main channel and a first and a second carrier channels configured to receive a hydrophobic fluid, the microfluidic device further comprising a first and a second inlet channels coupled to the main channel at a region upstream from the droplet generation zone;

providing a first reactant in fluid communication with the first inlet channel, the first reactant comprising a cationic lipid;

providing a second reactant in fluid communication with the second inlet channel, the second reactant comprising a nucleic acid;

providing a hydrophobic fluid in fluid communication with the first and second carrier channels;

flowing the first and second reactants and the hydrophobic fluid into the droplet generation zone to form aqueous droplets;

mixing the aqueous droplets containing the cationic lipid and the nucleic acid by passing the same in a single direction through a mixing region downstream of the droplet generation zone, the mixing region comprising a sawtooth-shaped channel configured to induce convective flow inside the droplets, wherein said mixing generates a plurality of aqueous droplets containing a plurality of monodisperse lipoplex assemblies; and splitting the generated aqueous droplets into a plurality of smaller sized aqueous droplets containing plurality of monodisperse lipoplex assemblies having substantially the same number of cationic lipid and nucleic acid molecules in a single droplet that is generally electrically neutral.

2. The method of claim 1, wherein the nucleic acid comprises DNA.

3. The method of claim 1, wherein the hydrophobic fluid comprises oil.

4. The method of claim 1, wherein the splitting is accomplished using a plurality of branch channels.

5. The method of claim 4, further comprising delivering the smaller sized aqueous droplets containing a plurality of monodisperse lipoplex assemblies into a common incubation chamber coupled to each branch channel.

6. The method of claim 4, further comprising splitting the already-split aqueous droplets containing a plurality of monodisperse lipoplex assemblies into a plurality of yet smaller sized aqueous droplets containing a plurality of monodisperse lipoplex assemblies.

7. The method of claim 6, wherein the yet smaller sized aqueous droplets containing a plurality of monodisperse lipoplex assemblies have volumes less than about 50 picoliters.

8. The method of claim 6, wherein the splitting is accomplished using a plurality of secondary branch channels.

9. The method of claim 6, further comprising extracting the plurality of monodisperse lipoplex assemblies of uniform size of less than 500 nm from the yet smaller sized aqueous droplets.

10. The method of claim 1, wherein the cationic lipid comprises N-[1-(2,3-dioleyloxy) propyl]-N,N,N-trimetylammonium chloride/1,2-Dioleoyl-sn-glycero-phosphatidylethanolamin (DOTMA/DOPE) in a 1:1 (weight/weight) ratio.

* * * * *